United States Patent [19]
Buurman

[11] Patent Number: 5,183,657
[45] Date of Patent: Feb. 2, 1993

[54] ANTIBODIES FOR USE IN ANTILYMPHOCYTE ANTIBODY THERAPY

[75] Inventor: Wim Buurman, Maastricht, Netherlands

[73] Assignee: Celltech Limited, Berkshire, United Kingdom

[21] Appl. No.: 881,317

[22] PCT Filed: Mar. 13, 1989

[86] PCT No.: PCT/GB89/00254
§ 371 Date: Oct. 22, 1990
§ 102(e) Date: Oct. 22, 1990

[87] PCT Pub. No.: WO89/08460
PCT Pub. Date: Sept. 21, 1989

Related U.S. Application Data

[63] Continuation of Ser. No. 585,065, Oct. 22, 1990, abandoned.

[30] Foreign Application Priority Data

Mar. 11, 1988 [GB] United Kingdom ............... 8805792

[51] Int. Cl.$^5$ ........................................... A61K 39/395
[52] U.S. Cl. .................................................. 424/85.8
[58] Field of Search ....................................... 424/85.8

[56] References Cited

FOREIGN PATENT DOCUMENTS 218868 9/1987 European Pat. Off. .

OTHER PUBLICATIONS

Chemical Abstracts, abstract 154301t, vol. 106, 1987.
Robinson, Muromonab-CD3 (Orthoclone OKT3-®)-A Review, Drugs of Today, pp. 603-609, vol. 22, No. 12, 1986.
Debets et al Transplantation, vol. 47, No. 3 pp. 487-492, Mar. 1989.
Tracey et al Nature, vol. 330 Dec. 17, 1987 pp. 662-664.

Primary Examiner—Lester L. Lee
Assistant Examiner—Choon P. Koh
Attorney, Agent, or Firm—Nixon & Vanderhye

[57] ABSTRACT

The use of antibodies against human alpha tumor necrosis factor in antilymphocyte antibody therapy is described. The anti-human alpha tumor necrosis factor antibodies may be used to prevent or treat shock-related conditions arising from antilymphocyte antibody therapy. Also described are compositions containing anti-human alpha tumor necrosis factor antibodies and anti-lymphocyte antibodies, as well as recombinant anti-human alpha tumor necrosis factor antibodies.

8 Claims, No Drawings

ANTIBODIES FOR USE IN ANTILYMPHOCYTE ANTIBODY THERAPY

This is a continuation of application Ser. No. 07/585,065, filed Oct. 22, 1990, now abandoned.

FIELD OF THE INVENTION

This invention relates to antibodies against human alpha (α)-tumour necrosis factor for use in antilymphocyte antibody therapy, to therapeutic compositions containing an antibody against human α-tumour necrosis factor and an antilymphocyte antibody, and to recombinant antibodies against human α-tumour necrosis factor.

BACKGROUND TO THE INVENTION

Antilymphocyte antibody therapy has become a recognised clinical technique for use when it is desired to supplement or modify the normal immune response in humans. Thus, for example, the intravenous administration of polyclonal rabbit or horse antilymphocyte antibodies is an effective treatment for acute kidney allograft rejection. More recently, monoclonal antilymphocyte antibodies, such as Orthoclone OKT3, have been used for this purpose.

Despite the effectiveness of antilymphocyte antibody therapy, treatment has been hindered in many cases by the occurence of shock-related side effects, making it necessary to temporarily discontinue the antibody infusion. Side effects include fever and chills, arthralgias, nausea and vomiting, tachycardia, angina pectoris, dyspnoea due to bronchospasm, and, in the case of OKT3 infusion, pulmonary oedema. In addition to the discomfort these side effects can cause, the severity of some of the effects precludes the use of antilymphocyte antibody therapy in some patients, for example people with pulmonary or cardiac disease.

We have now found that patients who are undergoing antilymphocyte antibody therapy, and who are also experiencing shock-related side effects, have surprisingly high plasma levels of α-tumour necrosis factor (α-TNF). We have used this to develop means to control shock-related conditions arising from antilymphocyte antibody therapy.

SUMMARY OF THE INVENTION

Thus, according to one aspect of the invention we provide an antibody against human α-tumour necrosis factor for use in the prevention or treatment of shock-related conditions arising from antilymphocyte antibody therapy.

The term antilymphocyte antibody therapy as used herein is especially to be understood to mean the use of an antilymphocyte antibody in the prophylaxis or treatment of immunoregulatory disorders in which rejection of self or non-self tissue occurs, for example in autoimmune diseases such as thyroiditis or rheumatoid arthritis, or, in particular, in a rejection episode following an organ or tissue transplant.

The shock-related conditions which may arise from antilymphocyte antibody therapy and which may be prevented or treated according to the present invention may be any physiological conditions which are generally associated with a degree of circulatory collapse. Particular conditions include, for example, cardiac conditions such as tachycardia and angina, e.g. angina pectoris; pulmonary conditions such as bronchospasm; musculo-skeletal conditions, for example joint pains such as arthralgia; and general metabolic disorders such as oedema, e.g. pulmonary oedema, and abnormal body temperatures.

The antibodies against human α-tumour necrosis factor (hereinafter referred to as anti-TNFα antibodies) for use according to the invention may in general belong to any immunoglobulin class. Thus for example the anti-TNFα antibody may be an immunoglobulin G or immunoglobulin M antibody.

The anti-TNFα antibody may be of animal, for example mammalian origin and may be for example of murine, rat or human origin. The antibody may be a whole immunoglobulin, or a fragment thereof, for example a fragment derived by proteolytic cleavage of a whole antibody, such as F(ab')$_2$, Fab' or Fab fragments, or fragments obtained by recombinant DNA techniques, for example Fv fragments (as described in International Patent Application No. PCT/GB 88/00747).

The anti-TNFα antibody may be polyspecific but is preferably monospecific for human α-TNF. The antibodies may be polyclonal or monoclonal antibodies. Particularly useful antibodies for use according to the invention include recombinant anti-TNFα antibodies and fragments thereof, i.e. anti-TNFα antibodies or fragments which have been produced using recombinant DNA techniques. Such recombinant anti-TNFα antibodies are novel compounds and form another aspect of the invention.

Especially useful recombinant antibodies include, (1) those having an antigen binding site at least part of which is derived from a different antibody, for example those in which the hypervariable or complementarity determining regions of one antibody have been grafted into the variable framework regions of a second, different antibody (as described in European Patent Specification No. 239400); (2) recombinant antibodies or fragments wherein non-Fv sequences have been substituted by non-Fv sequences from other, different antibodies (as described in European Patent Specifications Nos. 171496, 173494 and 194276); or (3) recombinant antibodies or fragments possessing substantially the structure of a natural immunoglobulin but wherein the hinge region has a different number of cysteine residues from that found in the natural immunoglobulin, or wherein one or more cysteine residues in a surface pocket of the recombinant antibody or fragment is in the place of another amino acid residue present in the natural immunoglobulin (as described in International patent Applications Nos. PCT/GB 88/00730 and PCT/GB 88/00729 respectively).

The anti-TNFα antibodies may be prepared using well-known immunological techniques employing α-TNF as antigen. Thus, for example, any suitable host may be injected with α-TNF and the serum collected to yield the desired polyclonal anti-TNFα antibody after appropriate purification and/or concentration, (for example by affinity chromatography using immobilised α-TNF as the affinity medium). Alternatively, splenocytes or lymphocytes may be recovered from the α-TNF-injected host and immortalised using for example the method of Kohler et al., Eur. J. Immunol. 6, 511, (1976), the resulting cells being segregated to obtain a single genetic line producing monoclonal anti-TNFα antibodies in accordance with conventional practice. Antibody fragments may be produced using conventional techniques, for example by enzymatic digestion of whole antibodies e.g. with pepsin [Parham, J.

Immunol., 131, 2895, (1983)] or papain [Lamoyi and Nisonoff, J. Immunol. Meth., 56, 235, (1983)]. Where it is desired to produce recombinant anti-TNFα antibodies these may be produced using for example the general methods described in the above-mentioned patent specifications.

In order to prevent or treat shock-related conditions arising from antilymphocyte antibody therapy, anti-TNFα antibodies may in general be administered in an appropriate form and amount at any suitable time before or during the therapy and, where necessary, after the therapy has finished. The anti-TNFα antibodies may be administered seperately or together with antilymphocyte antibodies.

Thus according to a further aspect of the invention we provide a two component system, each component for use in association with one another in antilymphocyte antibody therapy, said system comprising (1) a first component that is an anti-TNFα antibody, and (2) a second component that is an antilymphocyte antibody.

Where the anti-TNFα and antilymphocyte antibodies are administered separately, each may be formulated according to conventional practice. Thus, according to a further aspect of the invention, we provide a pharmaceutical composition comprising an anti-TNFα antibody together with one or more pharmaceutically acceptable carriers, excipients or diluents for use in the prevention or treatment of shock conditions arising from antilymphocyte antibody therapy.

The compositions according to this aspect of the invention may contain other active ingredients.

Where it is desired to administer the anti-TNFα and antilymphocyte antibody together, these may be conveniently formulated in the same composition. Thus according to a further aspect of the invention we provide a pharmaceutical composition which comprises an anti-TNFα antibody and an antilymphocyte antibody in admixture with one or more pharmaceutically acceptable carriers, excipients or diluents.

In yet a further aspect of the invention we provide a pharmaceutical composition which comprises an anti-TNFα antibody, and an antilymphocyte antibody in admixture with one or more pharmaceutically acceptable carriers, excipients or diluents, for use in antilymphocyte antibody therapy.

In a still further aspect of the invention, we provide a method for the manufacture of a pharmaceutical composition for use in the prevention or treatment of shock conditions arising from antilymphocyte antibody therapy which comprises admixing an anti-TNFα antibody and one or more pharmaceutically acceptable carriers, excipients or diluents.

In the compositions according to the invention the antilymphocyte antibody may be for example a polyclonal rabbit or horse antilymphocyte antibody, or a monoclonal antilymphocyte antibody such as Orthoclone OKT3. Such antibodies are readily available from known sources.

The compositions may take any suitable form for administration, and in particular will be in a form suitable for parenteral administration e.g. by injection or infusion, for example by bolus injection or continuous infusion. Compositions for injection or infusion may take such forms as suspensions, solutions or emulsions of the antibody in oily or aqueous vehicles, and, may contain formulatory agents such as suspending, stabilising and/or dispensing agents. Alternatively, the composition may be in a dry form, for reconstitution before use with an appropriate sterile liquid.

The dose at which the anti-TNFα antibody will be administered will depend on the nature of the antilymphocyte antibody therapy in use and whether the anti-TNFα antibody is being used prophylactically or to treat an existing shock-related condition arising from antilymphocyte antibody therapy. Thus, for example, the anti-TNFα antibody may be administered by infusion to a 70 kg man, usually at a total dose in the range 20-500 mg, over for example 2-3 days or for as long as the shock condition arising from the antilymphocyte antibody therapy persists.

Where the anti-TNFα antibody is infused concurrently with an antilymphocyte antibody, the antilymphocyte antibody may be infused at generally accepted doses depending on the antibody in use, for example with Orthoclone OKT3 at a dose of 5 mg/day for 10-14 days in a 70 kg man.

In a further aspect of the invention we provide a method of treatment of a human subject suffering from an immunoregulatory disorder which comprises administering effective amounts of an anti-TNFα antibody and an antilymphocyte antibody in association to the human subject.

Immunoregulatory disorders include, for example, those described above.

In another aspect of the invention we provide a method of treatment of a human subject suffering from a shock condition arising from antilymphocyte antibody therapy which comprises administering an effective amount of an effective amount of an anti-TNFα antibody to the human subject.

DESCRIPTION OF SPECIFIC EMBODIMENTS

Patients

Informed consent was obtained from seven consecutive kidney transplant patients, treated for acute allograft rejection with antithymocyte globulin (ATG) at the Maastricht University Hospital, to take serial blood samples for plasma tumour necrosis factor (TNF) measurement during ATG treatment. ATG treatment consisted of intravenous administration of 100-300 mg ATG together with 50 mg prednisolone in 500 ml saline, infused over a 8-hr period. All patients received 4 mg of the antihistamine chloropheniraminemaleate orally ½ hr before start of the infusion. EDTA-anticoagulated 5 ml blood samples were drawn from an intravenous line inserted in the arm opposite the one in which ATG was infused. Blood samples were immediately centrifuged and aliquots of plasma were stored at −70° C. for measurement of TNF concentration. During treatment patient temperature and blood pressure were monitored and the occurrence of other side effects of the treatment was registered.

Enzyme-linked Immunosorbent Assay (ELISA) for TNF

Plasma TNF concentrations were determined with a TNF-specific ELISA using monoclonal and polyclonal anti-TNF antibodies. Monoclonal antibodies were derived from anti-TNF secreting hybridomas obtained by a standard cell fusion procedure. Two different monoclonal antibodies were coated overnight at 4° C. in a flatbottom microtiter plate (Greiner, Nurtingen, FRG) at a final concentration of 5 ug Ig/ml. Plates were blocked with 1% (w/v) bovine serum albumin. Samples to be tested for TNF concentration were added to the wells and incubated for 1½ hrs. at room temperature. A standard titration curve was obtained by making serial dilutions of a known sample of recombinant TNF. The amount of TNF bound to the wells was quantitated by sequential incubation with a 1:2000 dilution of rabbit immune serum and a 1:5000 dilution of peroxidase conjugated goat anti-rabbit antibody (Jackson, West Grove, PA; antibody not crossreactive with human serum proteins), followed by adding substrate (o-phenylenediamine: Sigma, St. Louis, MO) to the wells. The colour reaction was stopped with 0.1M $H_2SO_4$ and absorption of light at 495 nm was measured with a microelisa autoreader (Flow, Irvine, UK). The lower detection limit of ELISA ranged between 5–10 pg/ml in plasma. TNF specific values were obtained by subtracting background absorptions due to non-TNF plasma proteins cross-linking in the ELISA, measured in the absence of either the monoclonal anti-TNF antibodies coated on the bottom of the ELISA plate or the second, rabbit anti-TNF antibodies. Plasma samples of a large group (n=60) of healthy volunteers were shown to be negative for TNF (i.e. <5 pg/ml) as determined with our assay.

In vitro Experiments

Peripheral blood mononuclear cells (PBMC) were prepared by buoyant density centrifugation on Lymphoprep (Nyegaard, Oslo, Norway) of buffy coats of donor blood. Monocytes were obtained by depleting PBMC of T-lymphocytes through rosetting with sheep red blood cells and centrifugation on Lymphoprep after which the interface layer cells were left to adhere to plastic for ½ hr at 37° C. After extensive washing, to remove non-adherent cells, the cells were shown to consist of more than 95% of esterase-positive cells. PBMC and monocytes were cultured in RPMI 1640 (Gibco, Paisley, Scotland) supplemented with 10% heat-inactivated (56° C., 20 min.) foetal calf serum (Boehringer, Mannheim, FRG) and 100 IU/ml penicillin and 100 ug/ml streptomycin (Flow, Irvine, UK). PBMC and monocytes were cultured in cluster wells (24-well plates, Greiner); In each well $2.5 \times 10^8$ PBMC and monocytes obtained after adherence of $2.5 \times 10^8$ T lymphocyte depleted PBMC per well were cultured in 600 ul medium. To these cultures different concentrations of ATG and of the anti-CD3 monoclonal antibody OKT3 (ascites derived from an OKT3-secreting hybridoma, purchased from the ATCC, Rockville, MD) were added and at different times samples of cell-free supernatant were harvested to measure TNF concentration. Lymphocyte proliferation was determined by measuring the incorporation of $^3H$-thymidine. 0.5 μCi $^3H$-thymidine (Amersham, UK; specific activity 5.0 Ci/mmol) was added to a sample of 100 μl of the cell cultures transferred into round-bottomed microtiter plates (Greiner) and after a 4 hour culture period the radioactivity incorporated in the cells was measured with a liquid scintillation counter.

TNF Levels in patients treated with ATG

All 7 patients treated for kidney graft rejection with ATG showed elevated plasma TNF levels, starting about 1 hour and reaching peak levels between 2–3 hrs after the start of the ATG infusion. Plasma TNF returned to zero level at about 6 hrs after the beginning of therapy. All patients developed a rise in body temperature shortly after plasma TNF had reached peak values. Body temperature normalized on the average 6 hr after TNF disappeared from the circulation. In most of the patients a slight rise in blood pressure accompanied with an increased heart rate was observed during the ATG infusion. All patients experienced mild to severe side effects, which coincided in time with the period of elevated plasma TNF levels, and which made it necessary to temporarily discontinue the ATG-infusion in several patients. In all patients symptoms waned shortly after TNF plasma levels has returned to normal. All patients experienced a feeling of great fatigue at the end of the therapy. Table I gives the relevant data on all 7 patients. Maxium plasma TNF concentrations in these patients ranged between 111 and 731 pg/ml on the first day of treatment. On the second day of treatment, when side effects of the ATG infusion were considerably less, maximum TNF levels were much lower, i.e. between 0 and 55 pg/ml.

TNF-production by peripheral blood mononuclear cells in vitro

In vitro experiments were performed in order to elucidate the cell source and mechanism of production of TNF in these patients. ATG or OKT3 was added at different concentrations to cultures of peripheral blood mononuclear cells (PBMC) and after a 6 hour culture period, TNF concentration in the supernatant was determined. Both ATG and OKT3 induced in a dose-related manner the release of TNF by PBMC in vitro. OKT3, which is a T-cell mitogen, also induced T-lymphocyte proliferation. However, ATG induced TNF secretion was not accompanied by T-lymphocyte proliferation, indicating that proliferation of T-lymphocytes is not a necessary prerequisite for TNF production in these cultures.

The kinetics of the ATG- and OKT3-induced release of TNF by PBMC was compatible with the rapid release of TNF in the circulation of the ATG-treated patients.

TABLE 1

Plasma TNF Concentrations And Other Relevant Data of ATG-treated Patients

| Patient* | treatment day | treatment | highest TNF conc. (pg/ml) | highest temp (°C.) | RR** (mm Hg) | symptoms |
|---|---|---|---|---|---|---|
| 1 m 33 yr | 1 | 300 mg ATG | 560 | 39.4 | +50/+5 | chills, vomiting |
| | 2 | 200 mg ATG | 55 | 37.9 | 0/0 | none |
| 2 f 54 yr | 1 | 100 mg ATG | 179 | 39.5 | +10/0 | chills, dyspnoea |
| 3 f 35 yr | 1 | 200 mg ATG | 111 | 39.0 | +5/+5 | chills |
| | 2 | 200 mg ATG | 24 | 38.0 | 0/0 | none |
| 4 m 49 yr | 1 | 200 mg ATG | 125 | 38.4 | −30/−20 | chills, dyspnoea, vomiting |

TABLE 1-continued

Plasma TNF Concentrations And Other Relevant Data of ATG-treated Patients

| Patient* | treatment day | treatment | highest TNF conc. (pg/ml) | highest temp (°C.) | RR** (mm Hg) | symptoms |
|---|---|---|---|---|---|---|
| | 2 | 200 mg ATG | 11 | 37.2 | 0/0 | none |
| 5 f 61 yr | 1 | 200 mg ATG | 138 | 38.2 | +15/0 | none |
| 6 f 54 yr | 1 | 200 mg ATG | 731 | 40.4 | +10/−10 | chills, dyspnoea, headache |
| | 2 | 100 mg ATG | 0 | 37.4 | 0/0 | none |
| 7 m 43 yr | 1 | 200 mg ATG | 593 | 39.5 | +15/−10 | chills, diarrhea, headache |

*m = male; f = female
**Expressed as difference between systolic/diastolic blood pressure measured before start of the ATG infusion and at the time of the highest plasma TNF concentration

I claim:

1. A pharmaceutical composition which comprises an antibody against human α-tumour necrosis and an antilymphocyte antibody in admixture with one or more pharmaceutically acceptable carriers, excipients or diluents.

2. A pharmaceutical composition according to claim 1 wherein the antilymphocyte antibody is a monoclonal antilymphocyte antibody.

3. A pharmaceutical composition according to claim 2 wherein the monoclonal antilymphocyte antibody is Orthoclone OKT3 TM.

4. A two component system, each component for use in association with one another in antilymphocyte antibody therapy, said system comprising (1) a first component that is an antinbody against human α-tumour necrosis factor, and (2) a second component that is an antilymphocyte antibody.

5. A method of treatment of a human subject suffering from an immunoregulatory disorder amenable to treatment by antilymphocyte antibody therapy which comprises administering to said human subject an effective amount of an anti-TNFα antibody in association with an antilymphocyte antibody.

6. A pharmaceutical composition according to any one of claims 1 to 3 wherein the antibody against human α tumor necrosis factor is recombinant α tumor necrosis factor.

7. A method of treatment of a human subject suffering from a shock condition arising from antilymphocyte antibody therapy which comprises administering an effective amount of an antibody against human α-tumor necrosis factor to the human subject.

8. A method for the prevention or treatment of shock-related conditions arising from antilymphocyte antibody therapy comprising administering to a person in need of same an effective amount of an antibody against human α-tumor necrosis factor.

* * * * *

UNITED STATES PATENT AND TRADEMARK OFFICE
CERTIFICATE OF CORRECTION

PATENT NO. : 5,183,657
DATED : September 3, 1992
INVENTOR(S) : Wim Buurman

It is certified that error appears in the above-indentified patent and that said Letters Patent is hereby corrected as shown below:

Column 7, Claim 1, Line 2, after "necrosis" insert —factor—.

Column 7, CLaim 4, Line 4, change "antinbody" to —antibody—.

Column 8, CLaim 6, Lines 3-4, after "is" delete "recombinant ∝ tumor necorsis factor" and insert —prepared by a recombinant DNA technique—.

Signed and Sealed this

Fourteenth Day of December, 1993

Attest:

BRUCE LEHMAN

*Attesting Officer*     *Commissioner of Patents and Trademarks*